United States Patent
Hu et al.

(10) Patent No.: US 7,504,558 B2
(45) Date of Patent: Mar. 17, 2009

(54) SOYBEAN ROOT-PREFERRED, NEMATODE-INDUCIBLE PROMOTER AND METHODS OF USE

(75) Inventors: Xu Hu, Johnston, IA (US); Guihua Lu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 75 days.

(21) Appl. No.: 11/556,211

(22) Filed: Nov. 3, 2006

(65) Prior Publication Data

US 2007/0192897 A1    Aug. 16, 2007

Related U.S. Application Data

(60) Provisional application No. 60/734,595, filed on Nov. 8, 2005.

(51) Int. Cl.
  *C12N 15/09* (2006.01)
  *C12N 15/82* (2006.01)
  *A01H 5/00* (2006.01)
  *A01H 5/10* (2006.01)

(52) U.S. Cl. .............. 800/287; 800/278; 800/298; 800/295; 800/320; 800/317; 800/301; 435/320.1; 435/468

(58) Field of Classification Search .......... None
  See application file for complete search history.

(56) References Cited

U.S. PATENT DOCUMENTS 6,271,437 B1 * 8/2001 Jessen et al. .......... 800/278

2004/0031072 A1 * 2/2004 La Rosa et al. .......... 800/278

FOREIGN PATENT DOCUMENTS

WO  WO99/28483    6/1999
WO  WO02/38588    5/2002

OTHER PUBLICATIONS

Kim et al. Plant Molecular Biology, 1994 vol. 24, pp. 105-117.*
Mahalingam, et al, Transcriptionally regulated genes in soybean-soybean cyst nematode interactions, , NCBI Genbank Accession No. AF127110, (1999).
Blanco-Portales, et al., A strawberry fruit-specific and ripening-related gene codes for a HyPRP protein involved in polyphenol anchoring, Plant Molecular Biology, (2004), 55:763-780.
Vaghchhipawala, et al., Soybean FGAM synthase promoters direct ectopic nematode feeding site activity, Genome, (2004), 47:404-413.

* cited by examiner

*Primary Examiner*—Medina A Ibrahim

(57) ABSTRACT

The present invention provides compositions and methods for regulating expression of heterologous nucleotide sequences in a plant. Compositions include a novel nucleotide sequence for a root-preferred and inducible promoter for the gene encoding a soybean ripening-related protein. A method for expressing a heterologous nucleotide sequence in a plant using the promoter sequences disclosed herein is provided. The method comprises stably incorporating into the genome of a plant cell a nucleotide sequence operably linked to the root-preferred promoter of the present invention and regenerating a stably transformed plant that expresses the nucleotide sequence.

24 Claims, No Drawings

SOYBEAN ROOT-PREFERRED, NEMATODE-INDUCIBLE PROMOTER AND METHODS OF USE

CROSS REFERENCE TO RELATED APPLICATIONS

This application claims the benefit of U.S. Provisional Application No. 60/734,595, filed on Nov. 8, 2005, which is herein incorporated by reference in its entirety.

FIELD OF THE INVENTION

The present invention relates to the field of plant molecular biology, more particularly to regulation of gene expression in plants.

BACKGROUND OF THE INVENTION

Recent advances in plant genetic engineering have enabled the engineering of plants having improved characteristics or traits, such as disease resistance, insect resistance, herbicide resistance, enhanced stability or shelf-life of the ultimate consumer product obtained from the plants and improvement of the nutritional quality of the edible portions of the plant. Thus, one or more desired genes from a source different than the plant, but engineered to impart different or improved characteristics or qualities, can be incorporated into the plant's genome. New gene(s) can then be expressed in the plant cell to exhibit the desired phenotype such as a new trait or characteristic.

The proper regulatory signals must be present and be in the proper location with respect to the gene in order to obtain expression of the newly inserted gene in the plant cell. These regulatory signals may include, but are not limited to, a promoter region, a 5' non-translated leader sequence and a 3' transcription termination/polyadenylation sequence.

A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce messenger RNA (mRNA) which serves as a template for translation of the RNA sequence into the amino acid sequence of the encoded polypeptide. The 5' non-translated leader sequence is a region of the mRNA upstream of the protein-coding region that may play a role in initiation and translation of the mRNA. The 3' transcription termination/polyadenylation signal is a non-translated region downstream of the protein coding region that functions in the plant cells to cause termination of the RNA transcript and the addition of polyadenylate nucleotides to the 3' end of the RNA.

Expression of heterologous DNA sequences in a plant host is dependent upon the presence of an operably linked promoter that is functional within the plant host. The type of promoter sequence chosen is based on when and where within the organism expression of the heterologous DNA is desired. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized.

An inducible promoter is a promoter that is capable of directly or indirectly activating transcription of one or more DNA sequences or genes in response to an inducer. In the absence of an inducer, the DNA sequences or genes will not be transcribed, or will be transcribed at a level lower than in an induced state. The inducer can be a chemical agent, such as a metabolite, growth regulator, herbicide or phenolic compound, or a physiological stress directly imposed upon the plant such as cold, drought, heat, salt, toxins. In the case of fighting plant pests, it is also desirable to have a promoter which is induced by plant pathogens, including plant insect pests, nematodes or disease agents such as a bacterium, virus or fungus. Contact with the pathogen will induce activation of transcription, such that a pathogen-fighting protein will be produced at a time when it will be effective in defending the plant. A pathogen-induced promoter may also be used to detect contact with a pathogen, for example by expression of a detectable marker, so that the need for application of pesticides can be assessed. A plant cell containing an inducible promoter may be exposed to an inducer by externally applying the inducer to the cell or plant such as by spraying, watering, heating, or by exposure to the operative pathogen.

A constitutive promoter is a promoter that directs expression of a gene throughout the various parts of a plant and continuously throughout plant development. Examples of some constitutive promoters that are widely used for inducing the expression of heterologous genes in transgenic plants include the nopaline synthase (NOS) gene promoter, from *Agrobacterium tumefaciens*, (U.S. Pat. No. 5,034,322), the cauliflower mosaic virus (CaMV) 35S and 19S promoters (U.S. Pat. No. 5,352,605), those derived from any of the several actin genes, which are known to be expressed in most cells types (U.S. Pat. No. 6,002,068), and the ubiquitin promoter, which is a gene product known to accumulate in many cell types.

Additional regulatory sequences upstream and/or downstream from the core promoter sequence may be included in expression constructs of transformation vectors to bring about varying levels of expression of heterologous nucleotide sequences in a transgenic plant. Genetically altering plants through the use of genetic engineering techniques to produce plants with useful traits thus requires the availability of a variety of promoters.

In order to maximize the commercial application of transgenic plant technology, it may be useful to direct the expression of the introduced DNA in a site-specific manner. For example, it may be useful to produce toxic defensive compounds in tissues subject to pathogen attack, but not in tissues that are to be harvested and eaten by consumers. By site-directing the synthesis or storage of desirable proteins or compounds, plants can be manipulated as factories, or production systems, for a tremendous variety of compounds with commercial utility. Cell-specific promoters provide the ability to direct the synthesis of compounds, spatially and temporally, to highly specialized tissues or organs, such as roots, leaves, vascular tissues, embryos, seeds, or flowers.

Alternatively, it may be useful to inhibit expression of a native DNA sequence within a plant's tissues to achieve a desired phenotype. Such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Of particular interest are promoters that are induced by plant pathogens. Pathogen infection, such as nematode infection, is a significant problem in the farming of many agriculturally significant crops. For example, soybean cyst nematode (*Heterodera glycines*, herein referred to as "SCN") is a widespread pest that causes substantial damage to soybeans every year. Such damage is the result of the stunting of the soybean plant caused by the cyst nematode. The stunted plants have smaller root systems, show symptoms of mineral deficiencies in their leaves, and wilt easily. The soybean cyst nematode is believed to be responsible for yield losses in soybeans that are estimated to be in excess of $1 billion per year in North America. Other pathogenic nematodes of significance to agriculture include the potato cyst nematodes *Globodera rostochiensis* and *Globodera pallida*, which are key pests of the potato, while the beet cyst nematode *Heterodera schachtii* is a major problem for sugar beet growers in Europe and the United States.

The primary method of controlling nematodes has been through the application of highly toxic chemical compounds. The widespread use of chemical compounds poses many problems with regard to the environment because of the non-selectivity of the compounds and the development of insect resistance to the chemicals. Nematicides such as Aldicarb and its breakdown products are known to be highly toxic to mammals. As a result, government restrictions have been imposed on the use of these chemicals. The most widely used nematicide, methyl bromide, is scheduled to be soon retired from use, and at present, there is no promising candidate to replace this treatment. Thus, there is a great need for effective, non-chemical methods and compositions for nematode control.

Various approaches to pest control have been tried including the use of biological organisms which are typically "natural predators" of the species sought to be controlled. Such predators may include other insects, fungi, and bacteria such as *Bacillus thuringiensis*. Alternatively, large colonies of insect pests have been raised in captivity sterilized and released into the environment in the hope that mating between the sterilized insects and fecund wild insects will decrease the insect population. While these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off of a plant or removed from a treated area by rain. Consequently, while the use of such biological controls has desirable characteristics and has met with some success, in practice these methods have not achieved the goal of controlling nematode damage to crops.

Advances in biotechnology have presented new opportunities for pest control through genetic engineering. In particular, advances in plant genetics coupled with the identification of insect growth factors and naturally-occurring plant defensive compounds or agents offer the opportunity to create transgenic crop plants capable of producing such defensive agents and thereby protect the plants against insect attack and resulting plant disease.

Additional obstacles to pest control are posed by certain pests. For example, it is known that certain nematodes, such as the soybean cyst nematode ("SCN"), can inhibit certain plant gene expression at the nematode feeding site (see Gheysen and Fenoll (2002) *Annu Rev Phytopathol* 40:191-219). Thus, in implementing a transgenic approach to pest control, an important factor is to increase the expression of desirable genes in response to pathogen attack. Consequently, there is a continued need for the controlled expression of genes deleterious to pests in response to plant damage.

One promising method for nematode control is the production of transgenic plants that are resistant to nematode infection and reproduction. For example, with the use of nematode-inducible promoters, plants can be genetically altered to express nematicidal proteins in response to exposure to nematodes. See, for example, U.S. Pat. No. 6,252,138, herein incorporated by reference. Alternatively, some methods use a combination of both nematode-inducible and nematode-repressible promoters to obtain nematode resistance. Thus, WO 92/21757, herein incorporated by reference, discusses the use of a two promoter system for disrupting nematode feeding sites where one nematode-inducible promoter drives expression of a toxic product that kills the plant cells at the feeding site while the other nematode-repressible promoter drives expression of a gene product that inactivates the toxic product of the first promoter under circumstances in which nematodes are not present, thereby allowing for tighter control of the deleterious effects of the toxic product on plant tissue. Similarly, with the use of proteins having a deleterious effect on nematodes, plants can be genetically altered to express such deleterious proteins in response to nematode attack.

Although these methods have potential for the treatment of nematode infection and reproduction, their effectiveness is heavily dependent upon the characteristics of the nematode-inducible or nematode-repressible promoters discussed above, as well as the deleterious properties of the proteins thereby expressed. Thus, such factors as the strength of such nematode-responsive promoters, degree of induction or repression, tissue specificity, or the like can all alter the effectiveness of these disease resistance methods. Similarly, the degree of toxicity of a gene product to nematodes, the protein's longevity after consumption by the nematode, or the like can alter the degree to which the protein is useful in controlling nematodes. Consequently, there is a continued need for the identification of nematode-responsive promoters and nematode-control genes for use in promoting nematode resistance.

SUMMARY OF THE INVENTION

Compositions and methods for regulating gene expression in a plant are provided. Compositions comprise novel nucleotide sequences for a root-preferred and inducible promoter that initiates transcription in response to wounding or feeding by nematode pests. More particularly, a transcriptional initiation region isolated from soybean is provided. Further embodiments of the invention comprise the nucleotide sequences set forth in SEQ ID NOs: 1-4, fragments of the nucleotide sequences set forth in SEQ ID NO: 1-4, and the plant promoter sequence deposited with the American Type Culture Collection (ATCC) on Aug. 30, 2005 as Patent Deposit No. PTA 6952, or fragments thereof. The embodiments of the invention further comprise nucleotide sequences having at least 85% sequence identity to the sequences set forth in SEQ ID NOs: 1-4, and which drive root-preferred, wound-inducible or nematode-inducible expression of an operably linked nucleotide sequence. Also included are functional fragments of the sequences set forth as SEQ ID NOs: 1-4 which drive root-preferred, wound-inducible or nematode-inducible expression of an operably linked nucleotide sequence.

Embodiments of the invention also include DNA constructs comprising a promoter operably linked to a heterologous nucleotide sequence of interest wherein said promoter is capable of driving expression of said nucleotide sequence in a plant cell and said promoter comprises one of the nucleotide sequences disclosed herein. Embodiments of the invention further provide expression vectors, and plants or plant cells having stably incorporated into their genomes a DNA construct mentioned above. Additionally, compositions include transgenic seed of such plants.

Method embodiments comprise a means for selectively expressing a nucleotide sequence in a plant, comprising transforming a plant cell with a DNA construct, and regenerating a transformed plant from said plant cell, said DNA construct comprising a promoter and a heterologous nucleotide sequence operably linked to said promoter, wherein said promoter initiates root-preferred, wound-inducible, or nematode-inducible transcription of said nucleotide sequence in a plant cell. In this manner, the promoter sequences are useful for controlling the expression of operably linked coding sequences in a root-preferred and/or inducible manner.

Downstream from and under the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a novel function or product in the plant. For example, a heterologous nucleotide sequence that encodes a gene product that confers herbicide, salt, cold, drought, pathogen, nematode or insect resistance, or other root traits such as nitrogen assimilation and utilization is encompassed. Furthermore, a heterologous nucleotide sequence that encodes a double-stranded RNA that confers herbicide, salt, cold, drought, pathogen, nematode or insect resistance, or one that impacts other root traits such as nitrogen assimilation and utilization is encompassed.

In a further embodiment, a method for modulating expression of a gene in a stably transformed plant is provided, comprising the steps of (a) transforming a plant cell with a DNA construct comprising the promoter of the embodiments operably linked to at least one nucleotide sequence; (b) growing the plant cell under plant growing conditions and (c) regenerating a stably transformed plant from the plant cell wherein expression of the nucleotide sequence alters the phenotype of the plant.

DETAILED DESCRIPTION OF THE INVENTION

The embodiments of the invention comprise novel nucleotide sequences for plant promoters, particularly a root-preferred, nematode-inducible, and wound-inducible promoter for a soybean ripening-related protein gene (hereinafter RRP gene), more particularly, the soybean RRP promoter. In particular, the embodiments provide for isolated nucleic acid molecules comprising the nucleotide sequence set forth in SEQ ID NOs: 1-4, and the plant promoter sequence deposited in a bacterial host as Patent Deposit No. PTA-6952, on Aug. 30, 2005, and fragments, variants, and complements thereof.

Plasmids containing the plant promoter nucleotide sequence (SEQ ID NO: 1) of the embodiments were deposited on Aug. 30, 2005 with the Patent Depository of the American Type Culture Collection (ATCC), at 10801 University Blvd., Manassas, Va. 20110-2209, and assigned Patent Deposit No. PTA-6952. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112. The deposit will irrevocably and without restriction or condition be available to the public upon issuance of a patent. However, it should be understood that the availability of a deposit does not constitute a license to practice the subject invention in derogation of patent rights granted by government action.

The promoter sequences of the embodiments are useful for expressing operably linked nucleotide sequences in an inducible manner, particularly in a root-preferred and nematode-inducible or wound-inducible manner. The sequences also find use in the construction of expression vectors for subsequent transformation into plants of interest, as probes for the isolation of other RRP gene promoters, as molecular markers, and the like.

The soybean RRP promoter of the embodiments was isolated from soybean genomic DNA. The specific method used to obtain the soybean RRP promoter of the present invention is described in the experimental section of this application.

The embodiments encompass isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The soybean RRP gene (SEQ ID NO: 7) is preferentially expressed in soybean root tissue and its expression was induced by nematode infection as indicated by Lynx Massively Parallel Signature Sequencing (MPSS) and Agilent microarray experiments which are further discussed in Example 1. The polypeptide encoded by the soybean RRP gene is presented as SEQ ID NO: 8. Ripening-related proteins (RRP) are found in ripening fruits, such as grapes and strawberries (See, for example, Davies C. and Robinson SP (2000) *Plant Physiology.* 122:803-812; Blanco-Portales R, et al. (2004). *Plant Mol Biol.* 55:763-80).

The soybean RRP promoter sequence directs expression of operably linked nucleotide sequences in a root-preferred and inducible manner. Therefore, RRP promoter sequences find use in the tissue-specific and inducible expression of an operably linked nucleotide sequence of interest. Particularly, the promoter of the embodiments acts to induce expression following the penetration and infection of a nematode or in response to wounding in plant roots.

The compositions of the embodiments include isolated nucleic acid molecules comprising the promoter nucleotide sequence set forth in SEQ ID NOs: 1-4. The term "promoter" is intended to mean a regulatory region of DNA usually comprising a TATA box capable of directing RNA polymerase 11 to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements such as those responsible for tissue and temporal expression of the coding sequence, enhancers, and the like. See particularly Australian Patent No. AU-A-77751/94 and U.S. Pat. Nos. 5,466,785 and 5,635,618. In the same manner, the promoter elements that enable tissue-specific or inducible expression can be identified, isolated, and used with other core promoters to confer inducible expression. In this aspect of the embodiments, a "core promoter" is intended to mean a basic promoter region that interacts with basic factors (such as TAT-binding protein and RNA polymerase II) without promoter upstream regulatory elements (Tian, R. (1995) *Scientific American* 1:54-61).

In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. Examples of suitable introns include, but are not limited to, the maize IVS6 intron, or potato LS1 INTRON2 (Vancanneyt, G., et al., (1990) *Mol Gen Genet.,* 220, 245-250). A regulatory element may also include those elements located downstream (3') to the site of transcription initiation, or within transcribed regions, or both. In the context of the present disclosure, a post-transcriptional regulatory element may include elements that are active following transcription initiation, for example translational and transcriptional enhancers, translational and transcriptional repressors, and mRNA stability determinants.

The regulatory elements, or fragments thereof, of the embodiments may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the embodiments may be operatively associated with constitutive, inducible, or tissue specific promoters or fragment thereof, to modulate the activity of such promoters within desired tissues within plant cells.

The soybean RRP promoter sequence, when assembled within a DNA construct such that the promoter is operably linked to a nucleotide sequence of interest, enables expression of the nucleotide sequence in the cells of a plant stably transformed with this DNA construct. The term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remains in the proper reading frame. In this manner, the nucleotide sequences for the promoters of the embodiments are provided in DNA constructs along with the nucleotide sequence of interest, typically a heterologous nucleotide sequence, for expression in the plant of interest. The term "heterologous nucleotide sequence" is intended to mean a sequence that is not naturally operably linked with the promoter sequence. While this nucleotide sequence is heterologous to the promoter sequence, it may be homologous, or native; or heterologous, or foreign, to the plant host.

It is recognized that the promoters of the embodiments may be used with their native coding sequences to increase or decrease expression, thereby resulting in a change in phenotype of the transformed plant.

Modifications of the isolated promoter sequences of the embodiments can provide for a range of expression of the heterologous nucleotide sequence. Thus, they may be modified to be weak promoters or strong promoters. Generally, a "weak promoter" is intended to mean a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

Fragments and variants of the disclosed promoter sequences are also encompassed by the embodiments. A "fragment" is intended to mean a portion of the promoter sequence. Fragments of a promoter sequence may retain biological activity and hence encompass fragments capable of driving inducible expression of an operably linked nucleotide sequence. Thus, for example, less than the entire promoter sequence disclosed herein may be utilized to drive expression of an operably linked nucleotide sequence of interest, such as a nucleotide sequence encoding a heterologous protein. Thus, SEQ ID NOs: 2, 3 and 4 are fragments, or truncations, of the promoter of SEQ ID NO: 1. Those skilled in the art are able to determine whether such fragments decrease expression levels or alter the nature of expression, i.e., constitutive or inducible expression. Alternatively, fragments of a promoter nucleotide sequence that are useful as hybridization probes, such as described below, may not retain this regulatory activity. Thus, fragments of a nucleotide sequence may range from at least about 20 nucleotides, about 50 nucleotides, about 100 nucleotides, and up to the full-length nucleotide sequences of the embodiments.

Thus, a fragment of a RRP promoter nucleotide sequence may encode a biologically active portion of the RRP promoter or it may be a fragment that can be used as a hybridization probe or PCR primer using methods disclosed below. A biologically active portion of a RRP promoter can be prepared by isolating a portion of the RRP promoter nucleotide sequence and assessing the activity of that portion of the RRP promoter. Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800, 900, 1000, 1100 or up to the number of nucleotides present in the full-length promoter nucleotide sequence disclosed herein, e.g. 1126 nucleotides for SEQ ID NO: 1.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol.* 155:335-350, and Erlich, ed. (1989) *PCR Technology* (Stockton Press, New York). Variants of these promoter fragments, such as those resulting from site-directed mutagenesis and a procedure such as DNA "shuffling", are also encompassed by the compositions of the embodiments.

An "analogue" of the regulatory elements of the embodiments includes any substitution, deletion, or addition to the sequence of a regulatory element provided that said analogue maintains at least one regulatory property associated with the activity of the regulatory element of the embodiments. Such properties include directing organ specificity, tissue specificity, or a combination thereof, or temporal activity, or developmental activity, or a combination thereof.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the embodiments will have at least 40%, 50%, 60%, 65%, 70%, 75%, 80%, 85%, 90%, 91%, 92%, 93%, 94%, to 95%, 96%, 97%, 98%, 99% or more sequence identity to that particular nucleotide sequence as determined by sequence alignment programs described elsewhere herein using default parameters. Biologically active variants are also encompassed by the embodiments. Biologically active variants include, for example, the native promoter sequences of the embodiments having one or more nucleotide substitutions, deletions, or insertions. Promoter activity may be measured by using techniques such as Northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050, herein incorporated by reference.

Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can be used to isolate corresponding sequences from other organisms, such as other plants, for example, other monocots. In this manner, methods such as PCR, hybridization, and the like can be used to identify such sequences based on their sequence homology to the sequence set forth herein. Sequences isolated based on their sequence identity to the entire RRP promoter sequence set forth herein or to fragments thereof are encompassed by the embodiments. The promoter regions of the embodiments may be isolated from any plant, including, but not limited to corn (*Zea mays*), Brassica (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, safflower, vegetables, ornamentals, and conifers.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, supra. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the RRP promoter sequence. Methods for preparation of probes for hybridization and for construction of cDNA and genomic libraries are generally known in the art and are disclosed in Sambrook, supra.

For example, the entire RRP promoter sequence disclosed herein, or one or more portions thereof, may be used as a probe capable of specifically hybridizing to corresponding RRP promoter sequences. To achieve specific hybridization under a variety of conditions, such probes include sequences that are unique among RRP promoter sequences and are generally at least about 10 nucleotides in length, including sequences of at least about 20 nucleotides in length. Such probes may be used to amplify corresponding RRP promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook supra).

Hybridization of such sequences may be carried out under stringent conditions. "Stringent conditions" or "stringent hybridization conditions" are conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, including those less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York), hereinafter "Ausubel". See also Sambrook supra.

Thus, isolated sequences that have inducible promoter activity and which hybridize under stringent conditions to the RRP sequences disclosed herein, or to fragments thereof, are encompassed by the embodiments.

In general, sequences that have promoter activity and hybridize to the promoter sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the algorithm of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997): and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Natl. Acad. Sci. USA* 89:10915).

Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN and the ALIGN PLUS programs are based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the web site for the National Center for Biotechnology Information on the world wide web. Alignment may also be performed manually by inspection.

Unless otherwise stated, sequence identity/similarity values provided herein refer to the value obtained using the GAP program with default parameters, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP.

The GAP program uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, at least 80%, at least 90%, or at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, and at least 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The RRP promoter sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid DNA construct that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the embodiments to comprise, for example, plant cells, protoplasts, tissues, callus, embryos as well as flowers, stems, fruits, ovules, leaves, or roots originating in transgenic plants or their progeny previously transformed with a DNA molecule of the embodiments, and therefore consisting at least in part of transgenic cells.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods disclosed herein is generally as broad as the class of higher plants amenable to transformation techniques, including both monocotyledonous and dicotyledonous plants.

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest for the embodiments include, for example, those genes involved in information, such as zinc fingers, those involved in communication, such as kinases, and those involved in housekeeping, such as heat shock proteins. More specific categories of transgenes, for example, include genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a plant, altering a plant's pathogen or insect defense mechanism, increasing the plant's tolerance to herbicides, altering plant development to respond to environmental stress, and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant.

It is recognized that any gene of interest can be operably linked to the promoter sequences of the embodiments and expressed in a plant.

A DNA construct comprising one of these genes of interest can be used with transformation techniques, such as those described below, to create disease or insect resistance in susceptible plant phenotypes or to enhance disease or insect resistance in resistant plant phenotypes. Accordingly, the embodiments encompass methods that are directed to protecting plants against fungal pathogens, bacteria, viruses, nematodes, insects, and the like. By "disease resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products.

Genes encoding disease resistance traits include detoxification genes, such as against fumonisin (U.S. Pat. No. 5,792, 931) avirulence (avr) and disease resistance (R) genes (Jones et al. (1994) *Science* 266:789; Martin et al. (1993) *Science* 262:1432; Mindrinos et al. (1994) *Cell* 78:1089); and the like. The RRP promoter of the embodiments may be used to express disease resistance genes in a root-preferred manner to prevent disease pathogens that typically infect plants through the roots. For example, *Phytophthora sojae* is a fungal pathogen that causes soybean root rot. At least 14 Rps genes at seven loci have been reported to provide resistance against 37 recorded *P. sojae* races in soybean cultivars (Kasuga T. et al. (1997) MPMI 10:1035-1044).

The RRP promoter of the embodiments may also be used to express genes in a root-preferred manner which may include, for example, insect resistance genes directed to those insects which primarily feed on the roots. Such insect resistance genes may encode resistance to pests that have great yield drag such as various species of rootworms, cutworms, and the like. Such genes include, for example, *Bacillus thuringiensis* toxic protein genes (U.S. Pat. Nos. 5,366,892; 5,747,450;

5,737,514; 5,723,756; 5,593,881; and Geiser et al. (1986) *Gene* 48:109); lectins (Van Damme et al. (1994) *Plant Mol. Biol.* 24:825); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Glyphosate resistance is imparted by mutant 5-enol pyruvylshikimate-3-phosphate synthase (EPSPS) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over-expression of genes encoding glyphosate N-acetyltransferase. See, for example, U.S. patent application Ser. Nos. 10/004,357; and 10/427,692.

Sterility genes can also be encoded in a DNA construct and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Agronomically important traits that affect quality of grain, such as levels and types of oils, saturated and unsaturated, quality and quantity of essential amino acids, levels of cellulose, starch, and protein content can be genetically altered using the methods of the embodiments. Modifications include increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference. Another example is lysine and/or sulfur rich seed protein encoded by the soybean 2S albumin described in U.S. Pat. No. 5,850,016, filed Mar. 20,1996, and the chymotrypsin inhibitor from barley, Williamson et al. (1987) *Eur. J. Biochem.* 165:99-106, the disclosures of which are herein incorporated by reference.

Exogenous products include plant enzymes and products as well as those from other sources including prokaryotes and other eukaryotes. Such products include enzymes, cofactors, hormones, and the like.

Examples of other applicable genes and their associated phenotype include the gene that encodes viral coat protein and/or RNA, or other viral or plant genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

In other embodiments of the present invention, the RRP promoter sequences are operably linked to genes of interest that improve plant growth or increase crop yields under high plant density conditions. For example, the RRP promoter may be operably linked to nucleotide sequences expressing agronomically important genes that result in improved primary or lateral root systems. Such genes include, but are not limited to, nutrient/water transporters and growth inducers. Examples of such genes, include but are not limited to, maize plasma membrane $H^+$-ATPase (MHA2) (Frias et al. (1996) *Plant Cell* 8:1533-44); AKT1, a component of the potassium uptake apparatus in *Arabidopsis* (Spalding et al. (1999) *J. Gen. Physiol.* 113:909-18); RML genes, which activate cell division cycle in the root apical cells (Cheng et al. (1995) *Plant Physiol.* 108:881); maize glutamine synthetase genes (Sukanya et al. (1994) *Plant Mol. Biol.* 26:1935-46); and hemoglobin (Duff et al. (1997) *J. Biol. Chem.* 27:16749-16752; Arredondo-Peter et al. (1997) *Plant Physiol.* 115: 1259-1266; Arredondo-Peter et al. (1997) *Plant Physiol.* 114: 493-500 and references cited therein). The RRP promoter is useful in expressing genes involved in nitrogen assimilation, such as ferredoxin sulfite oxidoreductase (Hirasawa, M. et al. (2004) *Biochim. Biophys. Acta,* 1608, 140-148.). The RRP promoter may also be useful in expressing antisense nucleotide sequences of genes that negatively affect root development under high-planting density conditions.

The heterologous nucleotide sequence operably linked to the RRP promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant.

"RNAi" refers to a series of related techniques to reduce the expression of genes (See for example U.S. Pat. No. 6,506, 559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The RRP promoter sequence of the embodiments, and its related biologically active fragments or variants disclosed herein, may be used to drive expression of constructs that will result in RNA interference including microRNAs and siRNAs.

In one embodiment of the invention, DNA constructs will comprise a transcriptional initiation region comprising one of the promoter nucleotide sequences disclosed herein, or variants or fragments thereof, operably linked to a heterologous nucleotide sequence whose expression is to be controlled by the inducible promoter of the embodiments. Such a DNA construct is provided with a plurality of restriction sites for insertion of the nucleotide sequence to be under the transcriptional regulation of the regulatory regions. The DNA construct may additionally contain selectable marker genes.

The DNA construct will include in the 5'-3' direction of transcription, a transcriptional initiation region (i.e., an inducible promoter of the embodiments), translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor 11 gene (Pinli) terminator is used. See, for example, Keil et al. (1986) *Nucl. Acids Res.* 14:5641-5650; and An et al. (1989) *Plant Cell* 1:1 15-122, herein incorporated by reference in their entirety.

The DNA construct comprising a promoter sequence of the embodiments operably linked to a heterologous nucleotide sequence may also contain at least one additional nucleotide sequence for a gene to be cotransformed into the organism. Alternatively, the additional sequence(s) can be provided on another DNA construct.

Where appropriate, the heterologous nucleotide sequence whose expression is to be under the control of the inducible promoter sequence of the embodiments and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The DNA constructs may additionally contain 5' leader sequences. Such leader sequences can act to enhance translation. Translation leaders are known in the art and include: picornavirus leaders, for example, EMCV leader (encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986) *Virology* 154:9-20); MDMV leader (Maize Dwarf Mosaic Virus); human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) *Molecular Biology of RNA*, pages 237-256); and maize chlorotic mottle virus leader (MCMV) (Lommel et al. (1991) *Virology* 81:382-385). See also Della-Cioppa et al. (1987) *Plant Physiology* 84:965-968. Other methods known to enhance translation and/or mRNA stability can also be utilized, for example, introns, such as the maize Ubiquitin intron (Christensen and Quail (1996) *Transgenic Res.* 5:213-218; Christensen et al. (1992) *Plant Molecular Biology* 18:675-689) or the maize AdhI intron (Kyozuka et al. (1991) *Mol. Gen. Genet.* 228:40-48; Kyozuka et al. (1990) *Maydica* 35:353-357), and the like.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the embodiments. Enhancers are known in the art and include the SV40 enhancer region, the 35S enhancer element, and the like.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites. Restriction sites may be added or removed, superfluous DNA may be removed, or other modifications of the like may be made to the sequences of the embodiments. For this purpose, in vitro mutagenesis, primer repair, restriction, annealing, re-substitutions, for example, transitions and transversions, may be involved.

Reporter genes or selectable marker genes may be included in the DNA constructs. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) *EMBO J.* 9:2517-2522; Kain et al. (1995) *BioTechniques* 19:650-655; and Chiu et al. (1996) *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481); phosphinothricin (DeBlock et al. (1987) *EMBO J.* 6:2513-2518).

Other genes that could serve utility in the recovery of transgenic events but might not be required in the final product would include, but are not limited to, examples such as GUS (b-glucuronidase; Jefferson (1987) *Plant Mol. Biol. Rep.* 5:387), GFP (green fluorescent protein; Chalfie et al. (1994) *Science* 263:802), luciferase (Riggs et al. (1987) *Nucleic Acids Res.* 15(19): 8115 and Luehrsen et al. (1992) *Methods Enzymol.* 216:397-414), and the maize genes encoding for anthocyanin production (Ludwig et al. (1990) *Science* 247:449).

The nucleic acid molecules of the embodiments are useful in methods directed to expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell. The methods of the embodiments are also directed to inducibly expressing a nucleotide sequence in a plant. Those methods comprise transforming a plant cell with a DNA construct comprising a promoter identified herein that initiates transcription in a plant cell in an inducible manner, operably linked to a heterologous nucleotide sequence, regenerating a transformed plant from said plant cell, and subjecting the plant to the required stimulus to induce expression.

The DNA construct comprising the particular promoter sequence of the embodiments operably linked to a nucleotide sequence of interest can be used to transform any plant. In this manner, genetically modified, i.e. transgenic or transformed, plants, plant cells, plant tissue, seed, root, and the like can be obtained.

Plant species suitable for the embodiments include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), oats (*Avena* spp.), sunflower (*Helianthus annuus*), safflower (*Carthamus tinctorius*), wheat (*Triticum aestivum*), barley (*Hordeum* spp.), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), onion (*Allium* spp.), dates (*Phoenix* spp.), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the embodiments involve introducing a nucleotide construct into a plant. As used herein "introducing" is intended to mean presenting to the plant the nucleotide construct in such a manner that the construct gains access to the interior of a cell of the plant. The methods of the embodiments do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

A "stable transformation" is one in which the nucleotide construct introduced into a plant integrates into the genome of the plant and is capable of being inherited by progeny thereof. "Transient transformation" means that a nucleotide construct introduced into a plant does not integrate into the genome of the plant.

The nucleotide constructs of the embodiments may be introduced into plants by contacting plants with a virus or viral nucleic acids. Generally, such methods involve incorporating a nucleotide construct of the embodiments within a viral DNA or RNA molecule. Methods for introducing nucleotide constructs into plants and expressing a protein encoded therein, involving viral DNA or RNA molecules, are known in the art. See, for example, U.S. Pat. No's. 5,889,191, 5,889, 190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,981, 840 and 5,563,055), direct gene transfer (Paszkowski et al. (1984) *EMBO J.* 3:2717-2722), and ballistic particle acceleration (see, for example, U.S. Pat. Nos. 4,945,050; 5,879, 918; 5,886,244; 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671 -674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having inducible expression of the desired phenotypic characteristic identified. Two or more generations may be grown to ensure that inducible expression of the desired phenotypic characteristic is stably maintained and inherited and then seeds harvested to ensure inducible expression of the desired phenotypic characteristic has been achieved. Thus as used herein, "transformed seeds" refers to seeds that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988). In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polypeptide is cultivated using methods well known to one skilled in the art.

The embodiments provide compositions for screening compounds that modulate expression within plants. The vectors, cells, and plants can be used for screening candidate molecules for agonists and antagonists of the RRP promoter. For example, a reporter gene can be operably linked to a RRP promoter and expressed as a transgene in a plant. Compounds to be tested are added and reporter gene expression is measured to determine the effect on promoter activity.

The following examples are offered by way of illustration and not by way of limitation.

EXPERIMENTAL

The embodiments are further defined in the following Examples, in which parts and percentages are by weight and degrees are Celsius, unless otherwise stated. Techniques in molecular biology were typically performed as described in Ausubel or Sambrook, supra. It should be understood that these Examples, while indicating embodiments of the invention, are given by way of illustration only. From the above discussion and these Examples, one skilled in the art can ascertain the essential characteristics of the embodiments, and without departing from the spirit and scope thereof, can make various changes and modifications of them to adapt to various usages and conditions. Thus, various modifications of the embodiments in addition to those shown and described herein will be apparent to those skilled in the art from the foregoing description. Such modifications are also intended to fall within the scope of the appended claims.

The disclosure of each reference set forth herein is incorporated herein by reference in its entirety.

EXAMPLE 1

Identification of the RRP Gene

The ripening-related protein (RRP) gene was identified as a root-preferred gene using a combination of Agilent microarray technology as well as Lynx Massively Parallel Signature Sequencing technology (MPSS™) (see Brenner S, et al. (2000) *Nature Biotechnology* 18:630-634, Brenner S et al. (2000) *Proc Natl Acad Sci USA* 97:1665-1670).

Agilent Microarray Analysis

The Agilent microarray experiments were carried out according to Agilent protocols (See: Agilent Technologies Laboratory Talk, "Industry-first 60-mer microarray kits", 11 Nov. 2002 . Retrieved from the internet <URL: http://www-.laboratorytalk.com/news/agi/agi212.html>) using soybean 60-mer gene chips.

Pioneer line YB17E and Bell seeds were planted in the greenhouse (grown at 26° C., with a 16 hour/8 hour light/dark cycle), and 10-day-old seeding roots were inoculated with 10,000 SCN race 3 eggs per 3 plants. Tissues were harvested 10 days after inoculation (See Table 1). The tissues were cleaned using tap water and frozen immediately in liquid nitrogen, and stored at −80° C. Total RNA was isolated for the microarray analysis.

TABLE 1

Tissues for Agilent microarray analysis

| Soybean line | Treatment | Tissues |
| --- | --- | --- |
| Bell | Uninfected | Stem + Leaf |
| Bell | Infected | Stem + Leaf |
| Bell | Uninfected | Root |
| Bell | Infected | Root |
| YB17E | Uninfected | Stem + Leaf |
| YB17E | Infected | Stem + Leaf |
| YB17E | Uninfected | Root |
| YB17E | Infected | Root |

Agilent microarray data enabled the selection of candidate genes which showed root-preferred expression and appeared to be induced by SCN infection. As shown in Table 2, the microarray data indicated that expression levels of the RRP gene in roots was 50-fold and 16-fold higher than in leaf and stem tissues in YB17E and Bell, respectively. These results clearly indicated RRP's root-preferred expression pattern. By comparing infected and uninfected tissues, it was clear that SCN induced RRP expression by 38% in the roots of YB17E and by 14% in the roots of Bell. In the leaf tissues, RRP expression was induced in YB17E, but repressed in Bell.

TABLE 2

Microarray analysis of RRP gene expression

| | YB17E | Bell |
| --- | --- | --- |
| Root (Uninfected) | 46,210 | 22,259 |
| Leaf-Stem (Uninfected) | 925 | 1421 |

TABLE 2-continued

Microarray analysis of RRP gene expression

| | YB17E | Bell |
| --- | --- | --- |
| Root (Uninfected)/Leaf-Stem (Uninfected) | 50 | 16 |
| Root (Infected) | 63,694 | 25,294 |
| Leaf-Stem (Infected) | 1063 | 1192 |
| Root (Infected)/Leaf-Stem (Infected) | 60 | 21 |
| Root (Infected)/Root (Uninfected) | 1.4 | 1.1 |
| Leaf-Stem (Infected)/Leaf-Stem (Uninfected) | 0.2 | 0.8 |

Lynx MPSS Analysis

The MPSS technology involves the generation of 17 base signature tags from mRNA samples that have been reverse transcribed. The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS platform can be used to determine the expression pattern of a particular gene and its expression level in different tissues.

Soybean genotype Pioneer 93B82 was used for Lynx MPSS experiments. Pioneer line 93B82 seeds were planted in soil pods in the greenhouse and grown at 26° C., with a 16 hour/8 hour light/dark cycle. A total of 10 samples were collected (See Table 3). Taproot, trifoliate leaf, and stem were collected from V3 and V5 stages that are chosen to represent the vegetative developmental stages. The equal fresh-weight of the same tissue type from the two chosen stages were combined and ground in liquid nitrogen immediately following harvesting and stored at −80° C. The same procedure was followed for tissues collected in reproductive stages. Lateral root, trifoliate leaf, stem, and petiole were collected at R1 and R3 stages. R1 stage captures the important transition from vegetative growth to reproductive growth and R3 is important as pods are beginning to set, which is particularly significant for yield research. Since R2 has full bloom, flowers were collected at this stage. Pods were collected at R3 stage as it starts pod development. Seed samples were collected at major seed development stages of R4 and R5.

TABLE 3

Lynx MPSS Sample Description

| Tissue Type | Developmental Stage* | # Of Samples | Comments |
| --- | --- | --- | --- |
| Taproot | V2 and V5 | 1 | Whole taproot |
| Young leaf | V2 and V5 | 1 | All trifoliate leaves on a plant |
| Young stem | V2 and V5 | 1 | Whole stem |
| Lateral root | R1 and R3 | 1 | |
| Mature leaf | R1 and R3 | 1 | Trifoliate leaves from top 5 nodes |
| Mature stem | R1 and R3 | 1 | Stem from top 5 nodes |
| Petiole | R1 and R3 | 1 | Petiole from top 5 nodes |
| Flower | R2 | 1 | Open flowers |
| Pod | R3 | 1 | Whole pod |
| Seed | R4 and R5 | 1 | |

The Lynx experiment was carried out as described Brenner S, et al. (2000) *Nature Biotechnology* 18:630-634.

As shown in Table 4, the soybean RRP gene expresses primarily in tap and lateral roots.

TABLE 4

Expression pattern of RRP gene in Lynx MPSS analysis

| Tissue | Expression (ppm) |
| --- | --- |
| Lateral root | 4818 |
| Tap root | 5532 |
| Young stem | 32 |
| Mature stem | 0 |
| Young leaf | 0 |
| Mature leaf | 0 |
| Flower | 0 |
| Pod | 0 |
| Seed | 0 |
| Petiole | 0 |

The RRP gene was then searched using proprietary EST database information to look at the tissue distribution. The tissue distribution search revealed that there are a total of 71 EST clones in the soybean EST database that encode the RRP gene. Thirty-four of the 71 clones are from root cDNA libraries. These data also show RRP has a highly root-preferred expression pattern. Primers were then designed to isolate the RRP promoter.

EXAMPLE 2

Isolation of the RRP Promoter

Soybean Jack plants were grown in the greenhouse at 26° C., with a 16 hour/8 hour light/dark cycle. Leaf tissues from the Jack cultivar were used for promoter isolation. The leaf tissues were ground in liquid nitrogen and total RNA was isolated by the Tri-pure Method (Boehringer). Genomic DNA was then isolated using a DNeasy Plant mini kit (Qiagen) according to the manufacturer's instructions.

Promoter regions of the soybean RRP gene were isolated from soybean genomic DNA using Universal GenomeWalker Kit (Clontech) according to the manufacturer's instructions. Restriction digested genomic DNAs were ligated with an adaptor to construct pools of genomic DNA fragments for genome walking by PCR using a RRP-specific primer (SEQ ID NO: 5) and an adaptor primer (Clontech). PCR was performed in a total volume of 25 pL in a solution of: 10 mM Tris-HCL, pH 8.3; 1.5 mM $MgCl_2$; 50 mM KCl; 0.1 mM dNTPs; and 0.25 µM of each primer, as appropriate; and 0.5 Units of Advantage Genomic PCR polymerase mix (Clontech) or Pwo DNA polymerase (Boehringer) under the conditions described in the manufacturer's instructions. Genomic DNA and/or cDNA library mixtures were used as templates for PCR amplification.

Analysis of Amplified PCR Products:

Amplified PCR fragments with the expected sizes were individually sliced out of the gel for second round PCR re-amplification with same conditions as used in the initial PCR. For the second round of PCR, a nested adaptor primer (Clontech) and a second RRP specific primer (SEQ ID NO 6) were used. Each second round PCR product showing a single band with the expected size was cloned into a TA vector (Clontech) according to the suppliers instructions. Identified positive clones were selected for DNA sequencing using an Applied Biosystems 373A (ABI) automated sequencer. DNA sequence analysis was carried out with Sequencer (3.0). Multiple sequence alignments (ClustalW) of the DNA sequences were analyzed with the Curatool (CuraGen).

EXAMPLE 3

Preparation of Transgenic Soybean Plants

The soybean transgenic plants were generated according the following protocols.

Soybean embryogenic suspension cultures are transformed with recombinant DNA plasmids by particle gun bombardment. The following stock solutions and media are used for transformation and regeneration of soybean plants:

Stock Solutions

Sulfate 100× Stock: 37.0 g $MgSO_4.7H_2O$, 1.69 g $MnSO_4.H_2O$, 0.86 g $ZnSO_4.7H_2O$, 0.0025 g $CuSO_4.5H_2O$.

Halides 100× Stock: 30.0 g $CaCl_2.2H_2O$, 0.083 g KI, 0.0025 g $CoCl_2.6H_2O$,

P, B, Mo 100× Stock: 18.5 g $KH_2PO_4$, 0.62 g $H_3BO_3$, 0.025 g $Na_2MoO_4.2H_2O$ Fe EDTA 100× Stock: 3.724 g $Na_2EDTA$, 2.784 g $FeSO_4.7H_2O$.

2,4-D Stock: 10 mg/mL.

Vitamin B5 1000× Stock: 10.0 g myo-inositol, 0.10 g nicotinic acid, 0.10 g pyridoxine HCl, 1 g thiamine.

Media (Per Liter)

SB196: 10 mL of each of the above stock solutions, 1 mL B5 Vitamin stock, 0.463 g $(NH_4)_2 SO_4$, 2.83 g $KNO_3$, 1 mL 2,4-D stock, 1 g asparagine,10 g sucrose, pH 5.7.

SB103: 1 pk. Murashige & Skoog salts mixture, 1 mL B5 Vitamin stock, 750 mg $MgCl_2$ hexahydrate, 60 g maltose, 2 g gelrite, pH 5.7.

SB166: SB103 supplemented with 5 g per liter activated charcoal.

SB71-4: Gamborg's B5 salts (Gibco-BRL catalog No. 21153-028), 1 mL B5 vitamin stock, 30 g sucrose, 5 g TC agar, pH 5.7.

Soybean embryogenic suspension cultures were maintained in 35 mL liquid medium (SB196) on a rotary shaker (150 rpm) at 28° C. with fluorescent lights providing a 16-hour day/8-hour night cycle. Cultures were subcultured every 2 weeks by inoculating approximately 35 mg of tissue into 35 mL of fresh liquid media.

Soybean embryogenic suspension cultures were transformed by particle gun bombardment (see Klein et al. (1987) *Nature* 327:70-73) using a DuPont Biolistic PDS1000/He instrument.

The recombinant DNA plasmid containing the full length RRP promoter sequence (SEQ ID NO: 1) as well as recombinant DNA plasmids containing the three deletion constructs (SEQ ID NOs: 2-4) were used to demonstrate the expression pattern of the RRP promoter and its deletions. The recombinant DNA plasmid used to express RRP::GUS was on a separate recombinant DNA plasmid from the selectable marker gene. Both recombinant DNA plasmids were co-precipitated onto gold particles as follows. The DNAs in suspension were added to 50 µL of a 20-60 mg/mL 0.6 µm gold particle suspension and then combined with 50 µL $CaCl_2$ (2.5 M) and 20 µL spermidine (0.1 M) The mixture was pulse vortexed 5 times, spun in a microfuge for 10 seconds, and the supernatant removed. The DNA-coated particles were then washed once with 150 µL of 100% ethanol, pulse vortexed and spun in a microfuge again, and resuspended in 85 µL of anhydrous ethanol. Five µL of the DNA-coated gold particles were then loaded on each macrocarrier disk.

Approximately 150 to 250 mg of two-week-old suspension culture is placed in an empty 60 mm×15 mm petri plate and the residual liquid was removed from the tissue using a pipette. The tissue was placed about 3.5 inches away from a retaining screen and each plate of tissue was bombarded once. Membrane rupture pressure was set at 650 psi and the chamber was evacuated to −28 inches of Hg. Eighteen plates were bombarded, and, following bombardment, the tissue from each plate was divided between two flasks, placed back into liquid media, and cultured as described above.

Seven days after bombardment, the liquid medium was exchanged with fresh SB196 medium supplemented with 50 mg/mL hygromycin or 100 ng/mL chlorsulfuron, depending on the selectable marker gene used in transformation. The selective medium was refreshed weekly or biweekly. Seven weeks post-bombardment, green, transformed tissue was observed growing from untransformed, necrotic embryogenic clusters. Isolated green tissue was removed and inoculated into individual flasks to generate new, clonally-propagated, transformed embryogenic suspension cultures. Thus, each new line was treated as independent transformation event. These suspensions were then maintained as suspensions of embryos clustered in an immature developmental stage through subculture or were regenerated into whole plants by maturation and germination of individual somatic embryos.

Transformed embryogenic clusters were removed from liquid culture and placed on solid agar medium (SB166) containing no hormones or antibiotics for one week. Embryos were cultured at 26° C. with mixed fluorescent and incandescent lights on a 16-hour day: 8-hour night schedule. After one week, the cultures were then transferred to SB103 medium and maintained in the same growth conditions for 3 additional weeks. Prior to transfer from liquid culture to solid medium, tissue from selected lines was assayed by PCR for the presence of the chimeric gene. Somatic embryos became suitable for germination after 4 weeks and were then removed from the maturation medium and dried in empty petri dishes for 1 to 5 days. The dried embryos were then planted in SB71-4 medium and allowed to germinate under the same light and germination conditions described above. Germinated embryos were transferred to sterile soil and grown to maturity.

EXAMPLE 4

Activity of the Full Length RRP Promoter

The RRP promoter was evaluated in transgenic soybean plants using GUS as a reporter gene. A total of 39 T0 events (three plants per event) were stained in GUS solution for histochemical analysis. More than 70% of the positive events show very high activity in roots compared to leaves and stems. The activity in roots was about 30 times higher than that in leaves. There are a few events that have activity only in roots. The leaf activity is mainly in the leaf vein, and there is some activity in stems.

This data is consistent with the expression pattern expected from the RRP promoter and confirms its root-preferred expression pattern.

EXAMPLE 5

Activity of Promoter Deletion Constructs Compared to Full Length

Three deletion constructs of the RRP promoter were evaluated in transgenic soybean plants using GUS as a reporter gene.

A total of 15 T0 events (three plants per event) containing the first deletion (SEQ ID NO: 2) were stained in GUS solution for histochemical analysis. Ten of the 15 events were GUS-positive. All of the GUS positive events showed very high activity in roots compared to leaves/stems. The activity in roots was more than 30 times higher than that in leaves/stems. A few events showed activity only in roots. The activity of this construct is very similar to the full-length promoter in term of the specificity and strength. This indicates that the DNA fragment from −1126 to −864 has little impact on RRP activity.

A total of 15 T0 events (three plants per event) containing the second deletion (SEQ ID NO: 3) were stained in GUS solution for histochemical analysis. Nine of the 15 events were GUS-positive. All of the GUS positive events showed relatively high activity in roots compared to that in leaves/stems. The activity of this construct is somewhat weaker compared to the full-length promoter. This result indicates that the DNA fragment from −864 to −590 has impact on RRP activity in roots.

A total of 14 T0 events (three plants per event) containing the third deletion (SEQ ID NO: 4) were stained in GUS solution for histochemical analysis. Nine of the 14 events were GUS-positive. All of the events showed activity in roots, leaves, and stems. The activity of this construct is much weaker compared the full-length promoter. The root-preference was significantly reduced. This result indicates that the DNA fragment from −590 to −410 contains regulatory elements for constitutive activity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated promoter comprising a nucleotide sequence selected from the group consisting of:
   a) a nucleotide sequence comprising the sequence set forth in SEQ ID NOs: 1-4 or a full-length complement thereof;
   b) a nucleotide sequence comprising the plant promoter sequence of the plasmid deposited as Patent Deposit No. PTA-6952, or a full-length complement thereof; and
   c) a nucleotide sequence comprising a fragment of at least 410 nucleotides of a) or b), wherein said sequence initiates transcription in a plant cell.

2. A DNA construct comprising the promoter of claim 1 operably linked to a heterologous nucleotide sequence of interest.

3. A plant cell having stably incorporated into its genome the DNA construct of claim 2.

4. The plant cell of claim 3, wherein said plant cell is from a dicot.

5. The plant cell of claim 4, wherein said dicot is soybean.

6. A plant having stably incorporated into its genome the DNA construct of claim 2.

7. The plant of claim 6, wherein said plant is a dicot.

8. The plant of claim 7, wherein said dicot is soybean.

9. A transgenic seed of the plant of claim 6, wherein the seed comprises the DNA construct.

10. The plant of claim 6, wherein the heterologous nucleotide sequence of interest encodes a gene product or a double-stranded RNA that confers herbicide, salt, cold, drought, nematode, pathogen, or insect resistance or that alters nitrogen assimilation and utilization.

11. A method for expressing a nucleotide sequence in a plant, said method comprising introducing into a plant a DNA construct, said DNA construct comprising a promoter operably linked to a heterologous nucleotide sequence of interest, wherein said promoter comprises a nucleotide sequence selected from the group consisting of:
   a) a nucleotide sequence comprising the sequence set forth in SEQ ID NO: 1, SEQ ID NO: 2, SEQ ID NO: 3 or SEQ ID NO: 4;
   b) a nucleotide sequence comprising the plant promoter sequence of the plasmid designated as Patent Deposit No. PTA-6952; and
   c) a nucleotide sequence comprising a fragment of at least 410 nucleotides of a) or b), wherein said nucleotide sequence initiates transcription in said plant.

12. The method of claim 11, wherein said plant is a dicot.

13. The method of claim 12, wherein said dicot is soybean.

14. The method of claim 11, wherein the heterologous nucleotide sequence encodes a gene product or a double-stranded RNA that confers herbicide, salt, cold, drought, nematode, pathogen, or insect resistance or that alters nitrogen assimilation and utilization.

15. The method of claim 11, wherein said heterologous nucleotide sequence of interest is selectively expressed in the root.

16. A method for expressing a nucleotide sequence in a plant cell, said method comprising introducing into a plant cell a DNA construct comprising a promoter operably linked to a heterologous nucleotide sequence of interest, wherein said promoter comprises a nucleotide sequence selected from the group consisting of:
  a) a nucleotide sequence comprising the sequence set forth in SEQ ID NO: 1, SEQ ID NO: 2, SEQ ID NO: 3 or SEQ ID NO: 4;
  b) a nucleotide sequence comprising the plant promoter sequence of the plasmid designated as Patent Deposit No. PTA-6952; and
  c) a nucleotide sequence comprising a fragment of at least 410 nucleotides of a) or b), wherein said nucleotide sequence initiates transcription in said plant cell.

17. The method of claim 16, wherein said plant cell is from a dicot.

18. The method of claim 17, wherein said dicot is soybean.

19. The method of claim 16, wherein the heterologous nucleotide sequence encodes a gene product or a double-stranded RNA that confers herbicide, salt, cold, drought, nematode, pathogen, or insect resistance or that alters nitrogen assimilation and utilization.

20. A method for selectively expressing a nucleotide sequence in a plant root, said method comprising introducing into a plant cell a DNA construct, and regenerating a transformed plant from said plant cell, said DNA construct comprising a promoter and a heterologous nucleotide sequence operably linked to said promoter, wherein said promoter comprises a nucleotide sequence selected from the group consisting of:
  a) a nucleotide sequence comprising the sequence set forth in SEQ ID NO: 1, SEQ ID NO: 2, SEQ ID NO: 3 or SEQ ID NO: 4;
  b) a nucleotide sequence comprising the plant promoter sequence of the plasmid designated as Patent Deposit No. PTA-6952; and
  c) a nucleotide sequence comprising a fragment of of at least 410 nucleotides of a) or b), wherein said nucleotide sequence initiates transcription in said plant root.

21. The method of claim 20, wherein expression of said heterologous nucleotide sequence alters the phenotype of said plant.

22. The method of claim 21, wherein the plant is a dicot.

23. The method of claim 22 wherein the dicot is soybean.

24. The method of claim 20, wherein the heterologous nucleotide sequence encodes a gene product or double-stranded RNA that confers herbicide, salt, cold, drought, nematode, pathogen, or insect resistance or that alters nitrogen assimilation and utilization.

* * * * *

SEQUENCE LISTING

<160> NUMBER OF SEQ ID NOS: 8

<210> SEQ ID NO 1
<211> LENGTH: 1126
<212> TYPE: DNA
<213> ORGANISM: Glycine max
<220> FEATURE:
<221> NAME/KEY: misc_feature
<222> LOCATION: (0)...(0)
<223> OTHER INFORMATION: Full-length RRP Promoter

<400> SEQUENCE: 1

```
actatagggc acgcgtggtc gacggcccgg gctggtaaaa ctttgatttg gccgggagta      60
gtaggggcct aggggggtaag gtaactcgtt cgagaattgc tttgcagtgc gttcttccct    120
gaagttacga agaacaagag ataacgtgct agttccaatg attaatggtg gtaatgggta    180
acgtgttttg ctccactaat ttactaagga ttaaccttga atccttgtcg gttataccta    240
gcaatagaaa tttcctcagc atttatacac aagcgagctt tgctgagata atacatgaat    300
taaaaatctc caagccacct tgctaaatc gcataagcta agccaacgaa cggaattagt     360
ccatgtacaa atcaacaatc acaatttaac tttactaaac atcgcttaca attcttttat    420
atatttcaat ttttttaaag ctactatcac atttgaattt ttattttaaa tattatttat    480
accacgtgga taaataactg acacttattt tcactaacgg acatgtcagt gttttccatt    540
aacaattgga tggcatatta acaatggaca aaaatgatta atttttagaaa actaaaggac    600
taaagtgtga ttcaattttc ataaggacca aaattatata attactaaat gaaaagtgaa    660
ttgacgctta ttattttta taagaataca attgaaaaaa aattatcaag aagttttaca    720
ataatagata agcatagaaa taacattttt ctataaaagt aacaaaacaa aagaaacgca    780
gataatatta aaatttcaaa ttaagtaata aaatttatta attaaattgt aaaacttatt    840
actaaaaaaa ctcatactaa aaatataaaa actacaaatt tagtaacaac aaacttttat    900
ttttggcct ggaatatatg tctattacta aatttggaat atttaaaata aaatgattgg    960
gtactttttt ttccttgtag ggtattgaat atggacccca cactttaatt atttagttgt   1020
taggagtggg taaattatgg tcttttttaag tcacatttgt tcgcaatatt catccccatc   1080
tcccatcttt gtttgttcca tctcttgctt cttgcttcta ttacat                  1126
```

<210> SEQ ID NO 2
<211> LENGTH: 864
<212> TYPE: DNA
<213> ORGANISM: Glycine max
<220> FEATURE:
<221> NAME/KEY: misc_feature
<222> LOCATION: (0)...(0)
<223> OTHER INFORMATION: RRP-Deletion 1

<400> SEQUENCE: 2

```
ttatacacaa gcgagctttg ctgagataat acatgaatta aaaatctcca agccaccttt      60
gctaaatcgc ataagctaag ccaacgaacg gaattagtcc atgtacaaat caacaatcac    120
aatttaactt tactaaacat cgcttacaat tcttttatat atttcaattt ttttaaagct    180
actatcacat ttgaattttt attttaaata ttatttatac cacgtggata aataactgac    240
acttattttc actaacggac atgtcagtgt tttccattaa caattggatg gcatattaac    300
aatggacaaa aatgattaat tttagaaaac taaaggacta aagtgtgatt caattttcat    360
aaggaccaaa attatataat tactaaatga aaagtgaatt gacgcttatt attttttata    420
agaatacaat tgaaaaaaaa ttatcaagaa gttttacaat aatagataag catagaaata    480
acattttttct ataaaagtaa caaaacaaaa gaaacgcaga taatattaaa atttcaaatt    540
aagtaataaa atttattaat taaattgtaa aacttattac taaaaaaact catactaaaa    600
atataaaaac tacaaattta gtaacaacaa acttttattt tttggcctgg aatatatgtc    660
```

```
tattactaaa tttggaatat ttaaaataaa atgattgggt acttttttt ccttgtaggg      720 tattgaatat ggaccccaca ctttaattat ttagttgtta ggagtgggta aattatggtc      780
tttttaagtc acatttgttc gcaatattca tccccatctc ccatctttgt tgttccatc      840 tcttgcttct tgcttctatt acat                                            864

<210> SEQ ID NO 3
<211> LENGTH: 590
<212> TYPE: DNA
<213> ORGANISM: Glycine max
<220> FEATURE:
<221> NAME/KEY: misc_feature
<222> LOCATION: (0)...(0)
<223> OTHER INFORMATION: RRP-Deletion 2

<400> SEQUENCE: 3
cattaacaat tggatggcat attaacaatg gacaaaaatg attaatttta gaaaactaaa       60
ggactaaagt gtgattcaat tttcataagg accaaaatta tataattact aaatgaaaag      120
tgaattgacg cttattattt tttataagaa tacaattgaa aaaaaattat caagaagttt      180
tacaataata gataagcata gaaataacat ttttctataa aagtaacaaa acaaaagaaa      240
cgcagataat attaaaattt caaattaagt aataaaattt attaattaaa ttgtaaaact      300
tattactaaa aaaactcata ctaaaaatat aaaaactaca aatttagtaa caacaaactt      360 ttatttttg gcctggaata tatgtctatt actaaatttg gaatatttaa aataaaatga      420
ttgggtactt ttttttcctt gtagggtatt gaatatggac cccacacttt aattatttag      480
ttgttaggag tgggtaaatt atggtctttt taagtcacat ttgttcgcaa tattcatccc      540
catctcccat ctttgtttgt tccatctctt gcttcttgct tctattacat                 590

<210> SEQ ID NO 4
<211> LENGTH: 410
<212> TYPE: DNA
<213> ORGANISM: Glycine max
<220> FEATURE:
<221> NAME/KEY: misc_feature
<222> LOCATION: (0)...(0)
<223> OTHER INFORMATION: RRP-Deletion 3

<400> SEQUENCE: 4
tacaataata gataagcata gaaataacat ttttctataa aagtaacaaa acaaaagaaa       60
cgcagataat attaaaattt caaattaagt aataaaattt attaattaaa ttgtaaaact      120
tattactaaa aaaactcata ctaaaaatat aaaaactaca aatttagtaa caacaaactt      180 ttatttttg gcctggaata tatgtctatt actaaatttg gaatatttaa aataaaatga      240
ttgggtactt ttttttcctt gtagggtatt gaatatggac cccacacttt aattatttag      300
ttgttaggag tgggtaaatt atggtctttt taagtcacat ttgttcgcaa tattcatccc      360
catctcccat ctttgtttgt tccatctctt gcttcttgct tctattacat                 410

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 5
gtcacttgct gggaaaatca ccact                                            25
```

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 6

```
aagtaataga agcaagaagc aagag                                          25
```

<210> SEQ ID NO 7
<211> LENGTH: 769
<212> TYPE: DNA
<213> ORGANISM: Glycine max
<220> FEATURE:
<221> NAME/KEY: misc_feature
<222> LOCATION: (0)...(0)
<223> OTHER INFORMATION: RRP cDNA Contig
<220> FEATURE:
<221> NAME/KEY: CDS
<222> LOCATION: (49)...(507)

<400> SEQUENCE: 7

```
tgttccatct cttgcttctt gcttctatta cttgcttctt tcttcacc atg tca ctt     57
                                                    Met Ser Leu
                                                      1 gct ggg aaa atc acc act gaa att ggg gtt cat gca acc gct gca aag    105
Ala Gly Lys Ile Thr Thr Glu Ile Gly Val His Ala Thr Ala Ala Lys
  5                  10                  15 tgg ttc aac ctc ttt gca aca caa ctt cat cat gtt caa aac ctt act    153
Trp Phe Asn Leu Phe Ala Thr Gln Leu His His Val Gln Asn Leu Thr
 20                  25                  30                  35 gat aga gta cat gga acc aag ctg cat caa ggt gaa gac tgg cat cac    201
Asp Arg Val His Gly Thr Lys Leu His Gln Gly Glu Asp Trp His His
                 40                  45                  50 aac gag aca gtc aaa cac tgg act tat acc ata gat ggt aag gct aca    249
Asn Glu Thr Val Lys His Trp Thr Tyr Thr Ile Asp Gly Lys Ala Thr
 55                  60                  65 aca tgt ctg gag agt att gaa tcc att gat gaa cag aac aaa aca atc    297
Thr Cys Leu Glu Ser Ile Glu Ser Ile Asp Glu Gln Asn Lys Thr Ile
 70                  75                  80 acc tac aag ctc ttc agt gga gac att gat cat aag tat aag aaa ttt    345
Thr Tyr Lys Leu Phe Ser Gly Asp Ile Asp His Lys Tyr Lys Lys Phe
 85                  90                  95 aag ttc acc ttt caa gcc att gat aag gat caa ggc ggt gct ttt att    393
Lys Phe Thr Phe Gln Ala Ile Asp Lys Asp Gln Gly Gly Ala Phe Ile
100                 105                 110                 115 aaa tgg acg gtt gaa tat gaa agg ctt gct gag gag gtt gat cct cca    441
Lys Trp Thr Val Glu Tyr Glu Arg Leu Ala Glu Glu Val Asp Pro Pro
                120                 125                 130 tat gga tac atc gaa tac ctg cac aaa tgc act aaa gat att gat gtt    489
Tyr Gly Tyr Ile Glu Tyr Leu His Lys Cys Thr Lys Asp Ile Asp Val
                135                 140                 145 cat ctt ctc aaa gca tag ctctaaaagt tatgcactaa gaaataatgg            537
His Leu Leu Lys Ala *
            150 gcttggcctc tggataagtg cttatatgta taataatcgg tgtggagttt gacgagaagg   597 atgcttatat agatccttcc tttgtatgga ataaacttgg atatgcatgt cggtgatgtc   657 ttgtatgtgt taaattatat atgtggaagt gctcaacgtg atacatatga atattaatga   717 atgttttatg atcgattttg ctaagtaaaa aaaaaaaaaa aaaaaaaaaa aa           769
```

<210> SEQ ID NO 8

-continued

```
<211> LENGTH: 152
<212> TYPE: PRT
<213> ORGANISM: Glycine max
<220> FEATURE:
<221> NAME/KEY: PEPTIDE
<222> LOCATION: (0)...(0)
<223> OTHER INFORMATION: Translation of RRP cDNA Contig

<400> SEQUENCE: 8

Met Ser Leu Ala Gly Lys Ile Thr Thr Glu Ile Gly Val His Ala Thr
 1               5                  10                  15

Ala Ala Lys Trp Phe Asn Leu Phe Ala Thr Gln Leu His His Val Gln
            20                  25                  30

Asn Leu Thr Asp Arg Val His Gly Thr Lys Leu His Gln Gly Glu Asp
        35                  40                  45

Trp His His Asn Glu Thr Val Lys His Trp Thr Tyr Thr Ile Asp Gly
    50                  55                  60

Lys Ala Thr Thr Cys Leu Glu Ser Ile Glu Ser Ile Asp Glu Gln Asn
65                  70                  75                  80

Lys Thr Ile Thr Tyr Lys Leu Phe Ser Gly Asp Ile Asp His Lys Tyr
                85                  90                  95

Lys Lys Phe Lys Phe Thr Phe Gln Ala Ile Asp Lys Asp Gln Gly Gly
            100                 105                 110

Ala Phe Ile Lys Trp Thr Val Glu Tyr Glu Arg Leu Ala Glu Glu Val
        115                 120                 125

Asp Pro Pro Tyr Gly Tyr Ile Glu Tyr Leu His Lys Cys Thr Lys Asp
    130                 135                 140

Ile Asp Val His Leu Leu Lys Ala
145                 150
```